United States Patent
Fölling (10) Patent No.: US 8,922,638 B2
(45) Date of Patent: Dec. 30, 2014

(54) METHOD AND APPARATUS FOR THE MICROSCOPIC IMAGING OF A SAMPLE STRUCTURE

(75) Inventor: Jonas Fölling, Heidelberg (DE)

(73) Assignee: Leica Microsystems CMS GmbH, Wetzlar (DE)

(*) Notice: Subject to any disclaimer, the term of this patent is extended or adjusted under 35 U.S.C. 154(b) by 495 days.

(21) Appl. No.: 13/275,393

(22) Filed: Oct. 18, 2011

(65) Prior Publication Data
US 2012/0092479 A1 Apr. 19, 2012

(30) Foreign Application Priority Data

Oct. 19, 2010 (DE) .......................... 10 2010 038 265
Mar. 4, 2011 (DE) .......................... 10 2011 001 091

(51) Int. Cl.
| | | |
|---|---|---|
| *H04N 7/18* | (2006.01) | |
| *G01N 21/64* | (2006.01) | |
| *G02B 21/16* | (2006.01) | |
| *G02B 21/36* | (2006.01) | |
| *G02B 27/58* | (2006.01) | |

(52) U.S. Cl.
CPC ........ *G01N 21/6458* (2013.01); *G01N 21/6428* (2013.01); *G02B 21/16* (2013.01); *G02B 21/367* (2013.01); *G02B 27/58* (2013.01)
USPC ............................. 348/79; 382/128; 250/459.1

(58) Field of Classification Search
None
See application file for complete search history.

(56) References Cited

U.S. PATENT DOCUMENTS

| | | | |
|---|---|---|---|
| 2008/0182336 A1* | 7/2008 | Zhuang et al. ................ 436/172 |
| 2009/0134342 A1 | 5/2009 | Hell et al. | |
| 2010/0303386 A1 | 12/2010 | Enderlein | |
| 2011/0226965 A1* | 9/2011 | Wolleschensky et al. . 250/459.1 |

FOREIGN PATENT DOCUMENTS

| | | | |
|---|---|---|---|
| DE | 10 2006 021 317 B3 | | 10/2007 |
| DE | 10 2008 024 568 A1 | | 12/2009 |
| DE | 10 2008 059328 | | 6/2010 |
| DE | WO2010060545 | * | 6/2010 |
| WO | 2006/127692 A2 | | 11/2006 |
| WO | 2007/128434 A1 | | 11/2007 |

OTHER PUBLICATIONS

Neto, Miranda, et al. "Pearson's Correlation Coefficient for Discarding Redundant Information in Real Time Autonomous Navigation System." Oct. 2007. IEEE Int'l Conf. on Control Applications. pp. 426-431.*

(Continued)

*Primary Examiner* — Dave Czekaj
*Assistant Examiner* — Kyle Lotfi
(74) *Attorney, Agent, or Firm* — Hodgson Russ LLP (57) ABSTRACT

A method and an apparatus for imaging a sample structure (34) with a light microscope are described. The sample structure (34) is prepared with markers and an active marker subset is generated in that a part of the markers is brought into a state in which they can be imaged. When a predetermined activation state is present, the sample structure (34) is imaged onto an arrangement (40) of sensor elements which each generate an image signal, these image signals resulting in a single frame of the sample structure (34). The presence of a predetermined activation state is checked in that at least two test single frames are generated at an interval, and the respective change of the image signal between the two test single frames is detected. The presence of the predetermined activation state is determined when the detected changes of the image signals in their entirety exceed a quantity.

10 Claims, 5 Drawing Sheets

(56) References Cited

OTHER PUBLICATIONS

Lidke, K. A. et al., "Superresolution by localization of quantum dots using blinking statistics", Optics Express, Sep. 5, 2005, vol. 13, No. 18, pp. 7052-7062.

Qu, X. et al., "Nanometer-localized multiple single-molecule fluorescence microscopy", Proc. Natl. Acad. Sci., Aug. 3, 2004, vol. 101, No. 31, pp. 11298-11303.

Gordon, M. P. et al., "Single-molecule high-resolution imaging with photobleaching", Proc. Natl. Acad. Sci., Apr. 27, 2004, vol. 101, No. 17, pp. 6462-6465.

Ram, S. et al., "Beyond Raleigh's criterion: A resolution measure with application to single molecule microscopy", Proc. Natl. Acad. Sci., Mar. 26, 2006, vol. 103, No. 12, pp. 4457-4462.

Rust, M. J. et al., "Sub-diffraction-limit imaging by stochastic optical reconstruction microscopy (STORM)", Nature Methods, Oct. 2006, vol. 3, No. 10, pp. 793-795.

Marsh, R. J. et al., "Control of Single Molecule Fluorescence Dynamics by Stimulated Emission Depletion", Proc. of SPIE Conf. Nanocrystals, and Organic and Hybrid Nanomaterials, 2003, vol. 5222, pp. 78-86.

Hartmann, Th. et al., "Model for the off-time distribution in blinking quantum dots", Journal of Luminescence, 2011, vol. 131, pp. 379-381.

Geisler, C. et al., "Resolution of $\lambda/10$ in fluorescence microscopy using fast single molecule photo-switching", Applied Physics A, Jun. 1, 2007, vol. 88, pp. 223-226.

Patterson et al., Developing Photoactivated Localization Microscopy, Biomedical Imaging: From Nano to Macro, Apr. 1, 2007.

\* cited by examiner

METHOD AND APPARATUS FOR THE MICROSCOPIC IMAGING OF A SAMPLE STRUCTURE

CROSS REFERENCE TO RELATED APPLICATIONS

This application claims priority of German patent application number 10 2010 038 265.5 filed Oct. 19, 2010 and German patent application number 10 2011 001 091.2 filed Mar. 4, 2011, the entire disclosures of which are incorporated by reference herein.

FIELD OF THE INVENTION

The present invention relates generally to microscopic imaging.

BACKGROUND OF THE INVENTION

In the recent past, light microscopic imaging methods have been developed with which, based on a sequential, stochastic localization of individual markers, in particular fluorescence molecules, sample structures can be imaged that are smaller than the diffraction-dependent resolution limit of conventional light microscopes. Such methods are, for example, described in WO 2006/127692 A2; DE 10 2006 021 317 B3; WO 2007/128434 A1, U.S. 2009/0134342 A1; DE 10 2008 024 568 A1; "Sub-diffraction-limit imaging by stochastic optical reconstruction microscopy (STORM)", Nature Methods 3, 793-796 (2006), M. J. Rust, M. Bates, X. Zhuang; "Resolution of Lambda/10 in fluorescence microscopy using fast single molecule photo-switching", Geisler C. et al, Appl. Phys. A, 88, 223-226 (2007). This new branch of microscopy is also referred to as localization microscopy. The applied methods are known in the literature, for example, under the designations (F)PALM ((Fluorescence) Photoactivation Localization Microscopy), PALMIRA (PALM with Independently Running Acquisition), GSD(IM) (Ground State Depletion Individual Molecule return) Microscopy) or (F)STORM ((Fluorescence) Stochastic Optical Reconstruction Microscopy).

The new methods have in common that the sample structures to be imaged are prepared with markers that have two distinguishable states, namely a "bright" state and a "dark" state. When, for example, fluorescent dyes are used as markers, then the bright state is a state in which they are able to fluoresce and the dark state is a state in which they are not able to fluoresce. For imaging sample structures with a resolution that is higher than the conventional resolution limit of the imaging optical system, a small subset of the markers is repeatedly brought into the bright state. In the following, this subset is referred to as active subset. In this connection, the density of the markers forming the "active" subset is to be chosen such that the average distance of adjacent markers in the bright state and thus in the state in which they can be imaged by a light microscope is greater than the resolution limit of the imaging optical system. The markers forming the active subset are imaged onto a spatially resolving arrangement of sensor elements so that of each marker a light distribution in the form of a light spot is detected whose size is determined by the resolution limit of the optical system.

The present invention relates generally to microscopic imaging. When the density of the markers contained in the active subset is so low that the average distance of the markers, as explained above, exceeds a minimum distance predetermined by the resolution limit of the light microscopic imaging, then a desired activation state is present. This activation state guarantees that each light spot detected by the sensor element arrangement originates from exactly one activated marker.

Figure 1:
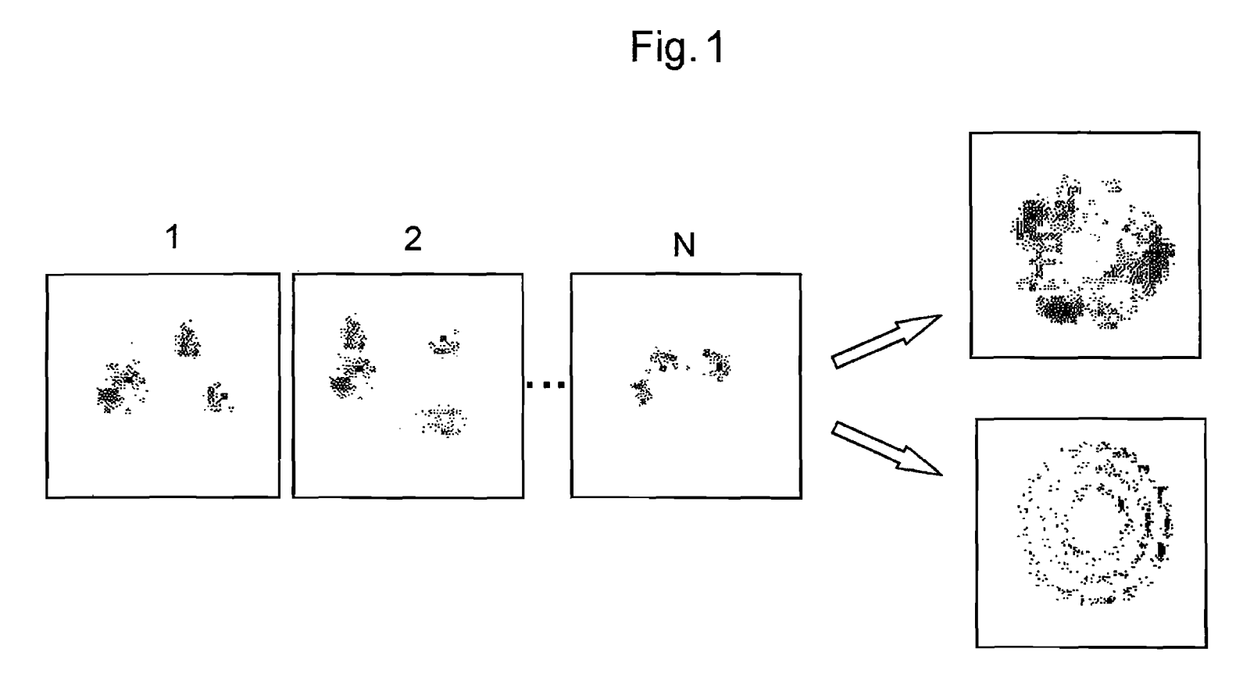
FIG. 1 shows a sequence of raw data single frames as well as a total image composed thereof before and after the determination of the centroids.

The above-explained method is illustrated in FIG. 1. In the left-hand side of FIG. 1, a sequence of raw data single frames is illustrated, which are numbered with 1, ..., N. Each of the light spots imaged in these raw data single frames originates from an active marker subset that is in the desired activation state, i.e. its marker density is so low that it is guaranteed that the average distance of the markers is greater than the minimum distance predetermined by the resolution limit of the light microscopic imaging.

In the upper right-hand part of FIG. 1, a total image is illustrated which results from the superimposition of raw data single frames 1, ..., N. This total image has a spread-out, spatially non-resolved light distribution which does not reproduce the sample structure to be imaged in detail.

In the lower right-hand part of FIG. 1, a total image is illustrated which results from the superimposition of centroids of the light distributions determined from the raw data single frames. This total image has a much higher resolution so that the sample structure can be well identified in detail—in the present example with its three concentric circular rings.

Figure 2:
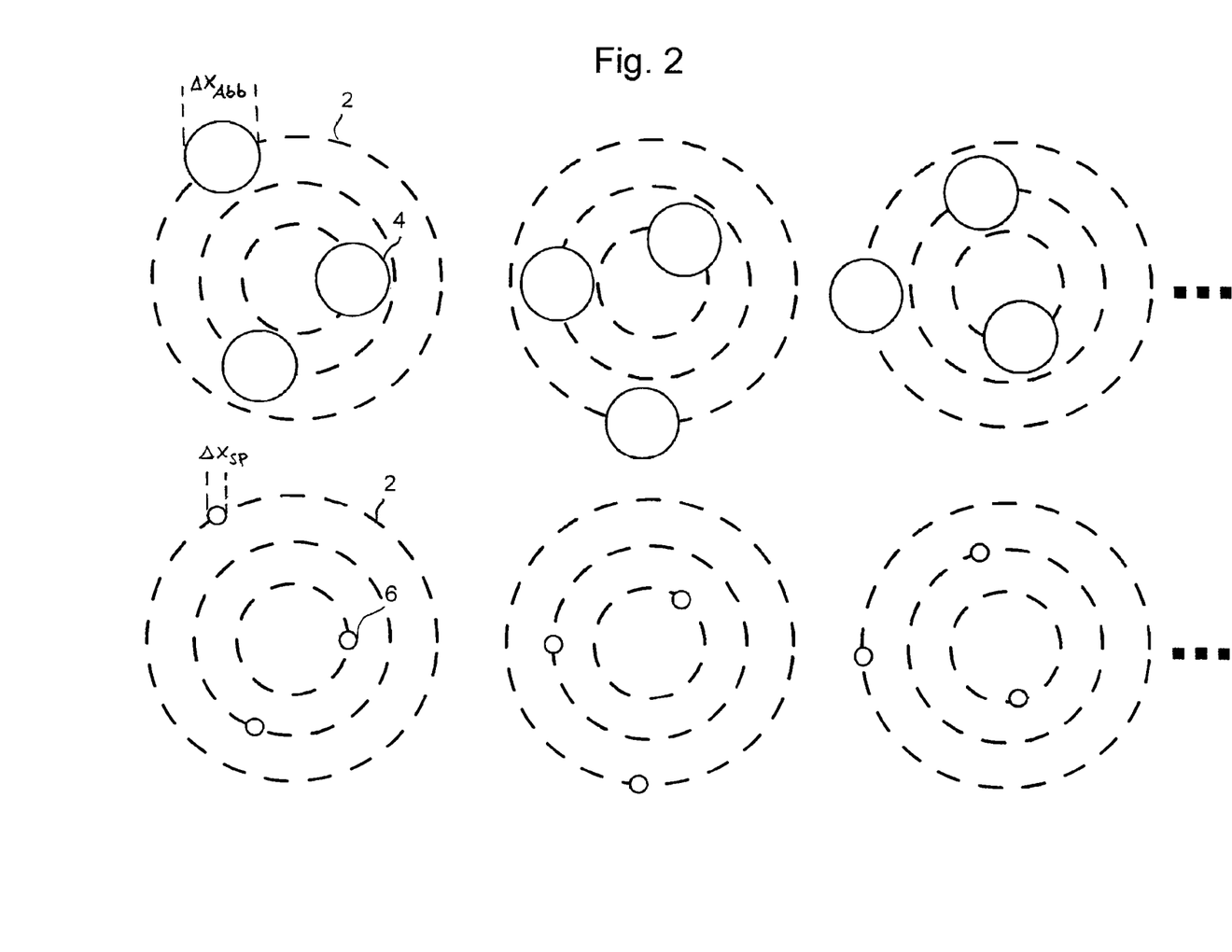
FIG. 2 shows a schematic illustration of the image sequence shown in FIG. 1 before and after the determination of the centroids.

For quantifying the localization precision which is to be achieved in the above-explained method, reference is made to FIG. 2 in which the situation shown in FIG. 1 is again illustrated merely schematically. In the upper part of FIG. 2, a sequence of raw data single frames is shown. The sample structure to be imaged, which is comprised of concentric circular rings, is illustrated in broken lines in FIG. 2 and is identified with the reference sign 2.

The individual markers of the active subset generate light distributions 4 whose size is determined by the resolution capability of the imaging optical system and is identified with $\Delta x_{Abb}$ in FIG. 2. As schematically illustrated in FIG. 2, the markers have an average distance to one another that is smaller than the size $\Delta x_{Abb}$ so that the light distributions 4 do not overlap.

In the lower part of FIG. 2, light distributions 6 are shown which result from the light distributions 4 obtained by the centroid determination. The achievable localization precision is given by the size $\Delta x_{SP}$ of the light distributions 6. For the localization precision $\Delta x_{SP}$ the following applies:

$$\Delta x_{SP} \alpha \frac{\Delta x_{Abb}}{\sqrt{n}}$$

wherein n denotes the number of photons detected per light distribution 4. The localization precision $\Delta x_{SP}$ is typically in a range of about 10 to 50 nm.

Prior to the capturing of a raw data single frame, the above-explained activation state is to be established. From which initial state this activation state is to be established, differs from method to method. Basically, two methods have to be distinguished, namely a method referred to as "bottom-up" method and a method referred to as "top-down" method. In the bottom-up method, at first all markers are in their dark state. The generation of the active marker subset as required for the high-resolution localization is achieved by an appropriate activation, e.g. by irradiation of activation light. This is for example the case for the (F)PALM method. In contrast thereto, in the top-down method at first all markers are in their bright state, i.e. their state in which they can be imaged by a light microscope. For generating the active marker subset, then most of the markers are brought into their dark state, again for example by irradiation of light. Here, the markers can be so-called "switchable" markers, e.g. switchable proteins. Likewise, these markers can, for example, be specific conventional fluorescent dyes which change into long-lived dark states, e.g. triplet states, when irradiated with excitation light (and thus are non-switchable markers in the true sense). For example, the GSD(IM) methods make use thereof.

Both in the bottom-up method and in the top-down method, it is relatively difficult to reproducibly establish the predetermined activation state which only makes the high resolution localization of the individual markers possible. In particular, it is not possible up to now to determine in an easy manner whether this predetermined activation state is present or not. Thus, it often occurs that too many of the markers are in their bright state so that the light distributions generated by the markers are not spatially separated from one another in the raw data single frames. This makes the light microscopic imaging of the sample structure more difficult, in particular the decision when the actual measuring can be started, i.e. when actually only so few markers are still in their bright state that the light distributions generated by the markers have, with a sufficiently high probability, a spatial distribution which makes a separate detection of the light distributions possible.

SUMMARY OF THE INVENTION

It is an object of the invention to develop the method for the light microscopic imaging of a sample structure such that it can be determined in an easy and precise manner whether the predetermined activation state in which the markers have a sufficiently long average distance from one another is present or not.

The invention solves this object, at least in part, by the presence of the predetermined activation state being checked in that at least two test single frames are generated at an interval, at least for a part of the sensor elements the respective change of the image signal between the two test single frames is detected, and the presence of the predetermined activation state is determined when the detected changes of the image signals in their entirety exceed a predetermined quantity.

The invention is based on the discovery that in a state in which the light signals emitted by the markers are detected spatially separately the temporal change of these signals in their entirety is greater than in a case in which the light signals are not detected separately. In the first case, so to speak a blinking can be identified in the microscope image, which is consequently typical for the presence of the desired activation state of the markers. This blinking occurs in that markers randomly change again and again from their bright state, i.e. from their state in which they can be imaged by a light microscope, into their dark state (e.g. by photobleaching) and other markers change from their dark state into their bright state in which they again emit a certain number of photons before they again change into the dark state.

The invention uses the above-mentioned phenomenon to check whether the predetermined activation state is present or not. This is done in that at least two test single frames are captured at an interval and the change of the image signals generated by the sensor elements is determined as a measure of how distinct the above-explained blinking is. When the spatial density of the markers in the bright state is so high that the light signals emitted by the individual markers spatially overlap one another, then the blinking behavior is less distinct. The blinking behavior in the microscope image is the weaker, the more markers emit their light signal onto one and the same sensor element. In that case, a temporal averaging of the light signals received by the individual sensor element takes place.

Thus, the invention intends to detect a measure for the blinking activity on the basis of the change between the two test single frames captured at an interval, and to decide on the basis thereof when the actual imaging of the sample structure can be started.

Preferably, on the basis of the detected changes of the image signals a temporal correlation of the corresponding image signals of the two test single frames is determined and the presence of the predetermined activation state is determined when the temporal correlation falls below a predetermined correlation threshold value. The temporal correlation of two successive single frames is a suitable measured quantity to determine the blinking activity and thus the presence of the desired activation state. The blinking activity is the higher, the lower the temporal correlation between the two test single frames.

In an advantageous development of the inventive method it is provided to allocate a first value to each of the detected image signals of the two test single frames when the detected image signals lie within a first value range and to allocate a second value different from the first value to each of the detected image signals of the two test single frames when the detected image signals lie within a second value range that is complementary to the first value range. For example, the value 0 can be allocated to image signals that are smaller than a predetermined threshold value, whereas the value 1 is allocated to image signals that are equal to or larger than this threshold value. From the two test single frames, thus data sets are derived which respectively only contain the values 1 and 0, and therefore are particularly well suited to, for example, detect the blinking activity by the determination of the temporal correlation.

The interval at which the two test single frames are generated is preferably set such that it is approximately equal to one to three times the average time period for which the markers remain in their state in which they can be imaged by a light microscope. As long as the interval is within this range, it is guaranteed that, when the predetermined activation state is present, a blinking activity which is sufficiently high and thus can be determined on the basis of the two test single frames is given.

Provided that the predetermined activation state is present, the activation state is preferably repeatedly checked while reducing the time interval at which the two test single frames are generated until the detected changes of the image signals in their entirety do no longer exceed the predetermined quantity, and the exposure time of the sensor elements is set taking into account the interval at which the detected changes of the image signals in their entirety no longer exceed the predetermined quantity. This preferred embodiment of the method thus provides to successively reduce, starting out from the desired activation state, the time interval at which the two test single frames are generated until the activation state is no longer present. By means of this approach, it is possible to find an exposure time as favorable as possible, namely a time which is as short as possible however as long as necessary to reliably detect the presence of an activation state.

As described at the beginning, normally an image sequence of a plurality of single frames is captured to image the sample structure. In this case, the inventive test step is carried out prior to the capturing of each single frame, i.e. the presence of the predetermined activation state is checked prior to the capturing of each single frame. Here, it is further advantageous to use the test single frames captured during one test step (if necessary in modified form) as single frames of the image sequence provided that the presence of the predetermined activation state has been determined in this test step. It is likewise possible to use only one of the test single frames as a single frame of the image sequence.

BRIEF DESCRIPTION OF THE DRAWINGS

Exemplary embodiments of the present invention are described in more detail below with reference to the schematic drawings, in which.

DETAILED DESCRIPTION OF THE INVENTION

Figure 3:
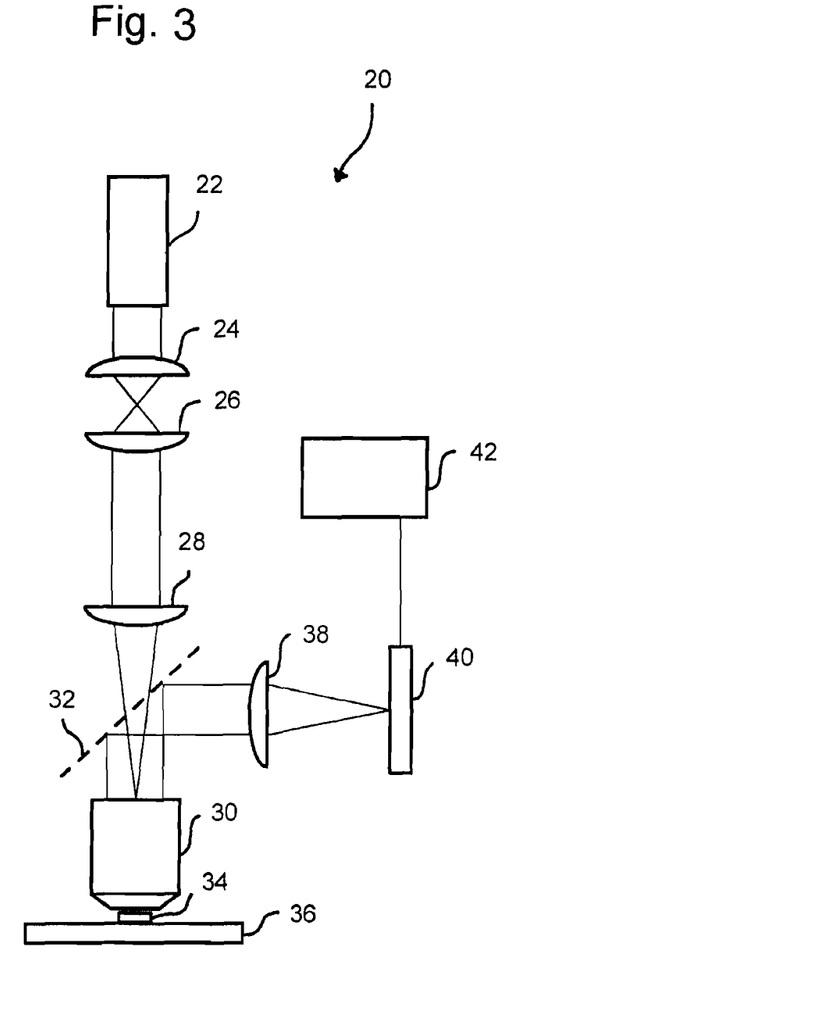
FIG. 3 shows the structure of a light microscope for implementing the method according to the invention.

FIG. 3 shows a light microscope 20 as an embodiment which is suitable for implementing the inventive method for the light microscopic imaging of a sample structure.

The light microscope 20 comprises a light source 22 which emits excitation light on a lens system comprised of two lenses 24 and 26. This lens system serves to collimate the excitation light emitted by the light source 22 in the desired manner. The collimated excitation light is then incident on a collecting lens 28. The collecting lens 28 focuses the excitation light into the aperture of the objective 30. Here, the excitation light at first passes through a dichroic minor 32 which is transparent to excitation light. The excitation light exiting from the objective 30 is then incident on a sample structure 34 which is mounted on a slide 36.

The sample structure 34 is, as explained at the beginning, prepared with markers, e.g. fluorescence molecules. Here, the methods mentioned at the beginning may be used to bring a respective part of these markers into the bright state, i.e. the state in which they can be imaged by a light microscope, and thereby to generate an active subset.

The light emitted from the sample structure 34 passes through the objective 30 and is incident on the dichroic mirror 32. The dichroic minor 32 is designed such that it reflects light emitted from the sample structure 34 and thus directs it onto a lens 38 which focuses the light onto a spatially resolving light detector 40. The light detector 40 is formed by a matrix-like arrangement of sensor elements, e.g. CCD elements. Each of these sensor elements converts the light received by it into an electric image signal. The image signals are then output to a control unit 42. The control unit 42 controls the individual microscope components and in particular has the function to process the image signals received from the light detector 40.

Using the light microscope 20 shown in FIG. 3, the sample structure 34, as explained at the beginning with reference to FIG. 1, is imaged. Thus, a sequence of raw data single frames is captured, for each of which another active subset of markers is imaged. In an image analysis process, then in each raw data single frame the centroids of the light distributions are determined by the control unit 42, which centroids represent those markers that are in their bright state. The centroids of the light distributions determined from the raw data single frames are then combined to a highly resolved total image.

The method according to the invention now provides that prior to the generation of the respective raw data single frame it is checked whether the activation state required for the high-resolution light microscopic imaging is present, i.e. whether the markers contained in the respective active marker subset have an average distance from one another that is greater than the minimum distance predetermined by the resolution limit of the light microscopic imaging. This will be explained in the following with reference to the flow diagram according to FIG. 4.

Figure 4:
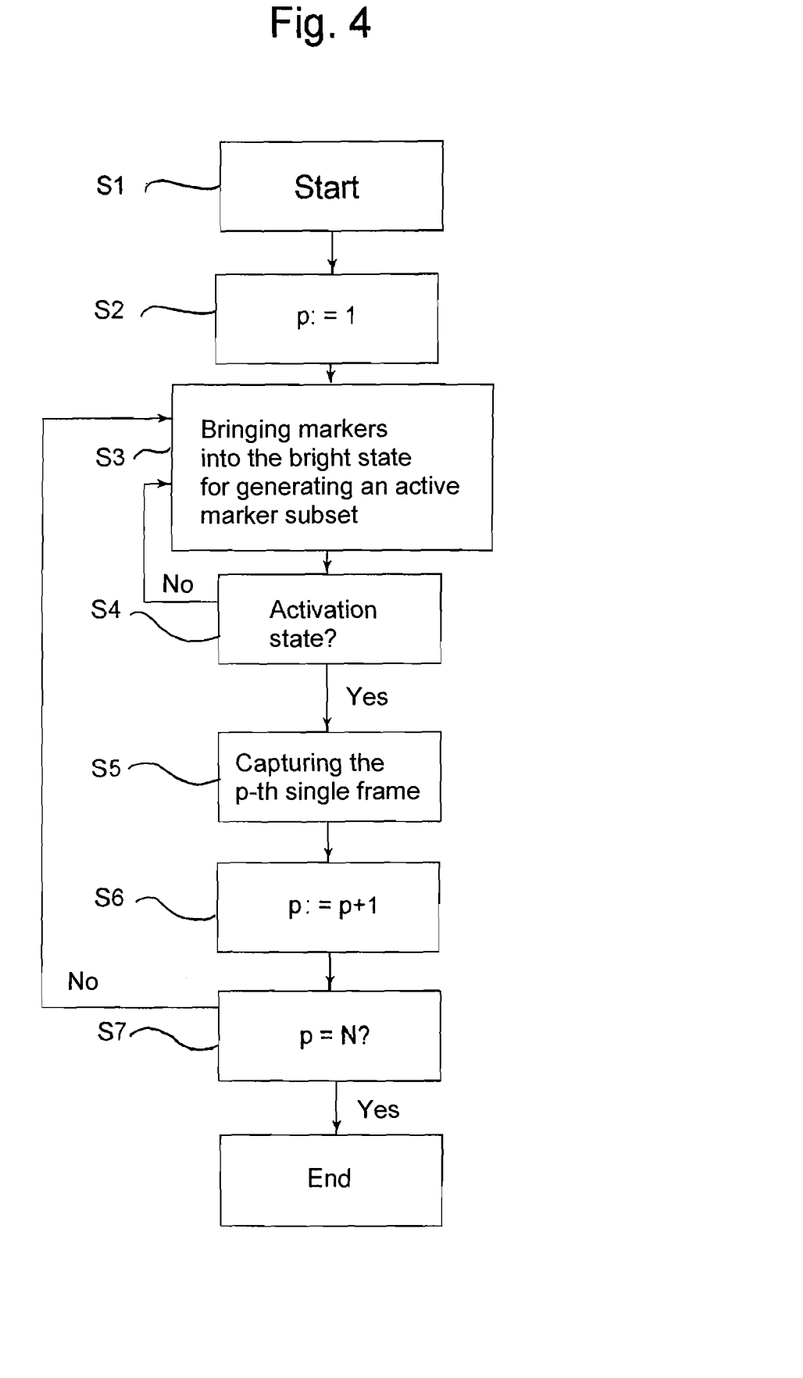
FIG. 4 shows a flow diagram for explaining the method according to the invention with reference to an embodiment.

The process illustrated in FIG. 4 starts with a step S1. In a step S2, a control variable p with which the raw data single frames are numbered is set to the value 1.

The loop which follows step S2 and is formed of steps S3 to S6 serves to generate the desired sequence of N single frames (p=1, . . . , N). Thus, when step S3 (p=1) is carried out for the first time for the raw data single frame to be generated as first raw data single frame, a part of the markers is brought into the state in which they can be imaged by a light microscope to generate a first active marker subset.

The invention now provides a check in step S4 as to whether the desired activation state is present, i.e. whether the markers contained in the first active marker subset have an average distance from one another that is greater than the minimum distance predetermined by the resolution limit of the light microscopic imaging. This inventive check will still be explained in detail further below. When the check in step S4 results that the predetermined activation state is present, then the process according to FIG. 4 is continued with step S5 in which the p-th raw data single frame is generated. Thereafter, in step S6, the control variable p is incremented by the value 1. If, however, it results in step S4 that the predetermined activation state is not present yet, then the process returns to step S3 in which another attempt is made to bring the markers with the desired spatial density into their state in which they can be imaged by a light microscope to thus establish the desired activation state. The loop formed of steps S3 and S4 is run through until the check in step S4 results that the predetermined activation state is present.

In step S7, it is checked each time whether the control variable p has already reached the total number N of single frames. If this is not the case, then the process returns to step S3. As soon as the control variable p has reached the value N, i.e. the desired number N of single frames is generated, the process shown in FIG. 4 is terminated.

As explained at the beginning, the centroids have to be determined in the raw data single frames to obtain the total image with the desired high resolution. In the present embodiment, the centroids can already be determined in step S4 or else only after termination of the process illustrated in FIG. 4.

In the following, the check of the activation state carried out in step S3 is explained in more detail.

For checking the activation state in step S3, at first two test single frames are captured in the form of two raw data single frames at an interval. In the present embodiment, this interval is defined by the exposure time which the light detector 40 requires for generating the image signals. This means that after generating the first raw data single frame the light detector 40 immediately starts generating the second raw data single frame. On the basis of these two test single frames, then the blinking activity is detected to determine whether the desired activation state is present or not.

In the present embodiment, the blinking activity is detected in that the temporal correlation of the two test single frames is determined. This is, for example, done according to the following relation:

$$k = \frac{\sum_{i,j} r_{ij}\tilde{r}_{ij}}{\sum_{i,j} r_{ij}^2} \approx \frac{\sum_{i,j} r_{ij}\tilde{r}_{ij}}{\sum_{i,j} \tilde{r}_{ij}^2}$$

in this relation, k denotes a correlation parameter, $r_{ij}$ denotes for the first captured test single frame of the two test single frames a signal value of the image signal of the sensor element that, in the matrix-like arrangement of the sensor elements forming the light detector 40, is located in the i-th row and the j-th column, wherein i=1, 2, ..., n and j=1, 2, ..., m and n denotes the total number of rows and m denotes the total number of columns. Accordingly, $\tilde{r}_{ij}$ denotes a signal value of the image signal of the sensor element arranged in the i-th row and the j-th column for the single frame of the two test single frames captured at a later point in time.

The above given relation expresses that for each sensor element, the signal values of the two test single frames are multiplied with one another and then this product is summed over all sensor elements. The sum obtained in this way is normalized in that it is divided by the sum of the squares of the signal values of one of the two test single frames. The correlation parameter k determined in this way then takes on a value between 0 and 1, i.e. 0≤k≤1. When the value k is close to the value 0, then the temporal correlation between the two test single frames is low, i.e. distinct changes occur between the two test single frames. This in turn means that the blinking activity is high and thus the desired activation state is present.

If, in contrast, the correlation parameter k is close to the value 1, then the temporal correlation is high and only slight changes occur between the two test single frames. This in turn means that the blinking activity is low. In this case, the spatial density of the markers which are in the state in which they can be imaged by a light microscope is still too high and has to be reduced further to achieve the desired localization precision.

In order to pass the decision as to whether the predetermined activation state is present or not, a threshold value between 0 and 1 is set in advance. If the correlation parameter k is smaller than this threshold value, then it is assumed that the blinking activity is sufficiently high and thus the predetermined activation state is present. If, in contrast, this is not the case, then the spatial density of the markers in the state in which they can be imaged by a light microscope should be reduced further.

In the present embodiment, the correlation parameter k is detected taking into account all sensor elements. However, it is likewise possible to only use a part of the sensor elements for determining the correlation parameter k.

The above given relation for determining the correlation parameter k assumes that a sensor element receiving no light emits an image signal having the value 0. If, however, there is background noise, i.e. if in this case the respective sensor element emits an image signal having a value greater than 0, then this can be taken into account in the above given formula in that the averaged background noise is deducted.

It is also possible to allocate either the value 1 or the value 0 to each of the signal values $r_{ij}$ and $\tilde{r}_{ij}$, dependent on whether these are greater than a predetermined threshold value or not. By this measure, one obtains data sets from each of the two test single frames that only have the values 0 and 1, which makes the determination of the correlation parameter k easier.

The threshold value with which the determined correlation parameter k is to be compared is preferably set dependent on an error tolerance to be defined for the individual case. What is understood by "error" is the detection of a light distribution that does not originate from a single marker but from several markers whose distance to one another is smaller than the minimum distance predetermined by the resolution limit of the light microscopic imaging.

Figure 5:
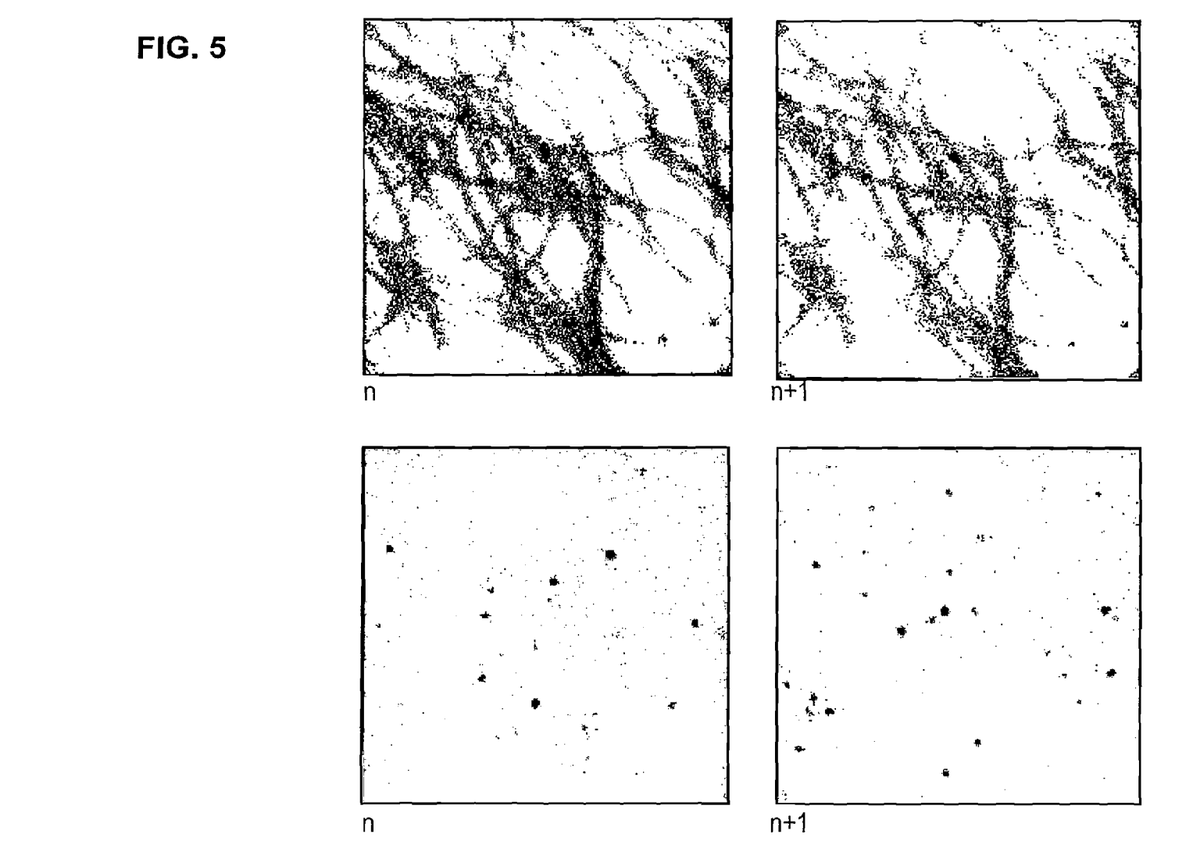
FIG. 5 shows two successive raw data single frames respectively in a case in which the predetermined activation state is not present and in a case in which the predetermined activation state is present.

In FIG. 5, practical examples are shown which illustrate the influence of the marker density on the raw data single frames. In these examples, microtubuli of PtK2 cells stained with Rh6G are imaged by a light microscope. Each time, two successive raw data single frames are illustrated.

In the two upper raw data single frames of FIG. 5, the density of markers in the state in which they can be imaged by a light microscope is too high, i.e. the desired activation state is not present. Accordingly, the two successively captured raw data single frames differ only slightly from each other.

In contrast, in the case of the two lower raw data single frames of FIG. 5, the density of markers in the state in which they can be imaged by a light microscope is so low that the desired activation state is present. As can be taken from a comparison of the two successively captured raw data single frames, individual markers can be detected in this activation state. Moreover, it becomes clear that markers which emit light signals in one of the two raw data single frames are mostly not detectable in the other raw data single frame (and vice versa). This means that when these raw data single frames are captured, the blinking activity is high.

The invention is not to be limited to the specific embodiments disclosed, and modifications and other embodiments are intended to be included within the scope of the invention.

What is claimed is:

1. A method of imaging a sample structure with a light microscope having a resolution limit, the method comprising the steps of:
    preparing the sample structure with markers configured to be brought into a state in which the markers are configured to be imaged by the light microscope;
    generating an active marker subset by bringing a portion of the markers into the state in which the markers are configured to be imaged by the light microscope;
    checking for presence of a predetermined activation state in which markers in the active marker subset have an average distance from one another greater than a minimum distance predetermined by the resolution limit of the light microscope by generating at least two test single frames at an interval, the at least two test single frames being captured by a plurality of sensor elements generating respective image signals, and comparing the at least two test single frames to one another in order to detect changes of corresponding image signals between the at least two test single frames, wherein the presence of the predetermined activation state is found if the detected changes of the image signals collectively exceed a predetermined quantity; and
    imaging the sample structure onto the plurality of sensor elements when the predetermined activation state is present, wherein the sensor elements generate respective image signals resulting in a single frame of a sample structure image.

2. The method according to claim 1, wherein the step of checking for the presence of the predetermined activation state includes determining a temporal correlation of the corresponding image signals of the two test single frames based on the detected changes of the image signals, wherein the presence of the predetermined activation state is found if the temporal correlation falls below a predetermined correlation threshold value.

3. The method according to claim 2, wherein the at least two test single frames includes a first captured test single frame and a second captured test single frame, the second captured test single frame being captured at a later point in time than the first captured test single frame, and wherein the plurality of sensor elements is a matrix array of sensor elements having n rows and m columns; and wherein the temporal correlation is determined according to the following relationship:

$$k = \frac{\sum_{i,j} r_{ij} \tilde{r}_{ij}}{\sum_{i,j} r_{ij}^2} \approx \frac{\sum_{i,j} r_{ij} \tilde{r}_{ij}}{\sum_{i,j} \tilde{r}_{ij}^2}$$

wherein:
k denotes a correlation parameter;
$r_{ij}$ denotes a signal value of the image signal of the sensor element located in the i-th row and the j-th column, wherein i=1, 2, ..., n and j=1, 2, ..., m for the first captured test single frame of the at least two test single frames; and
$\tilde{r}_{ij}$ denotes a signal value of the image signal of the sensor element located in the i-th row and the j-th column for the second captured test single frame.

4. The method according to claim 1, wherein a first value is allocated to each of the image signals of the at least two test single frames when the respective image signal lies within a first value range; and wherein a second value, different from the first value, is allocated to each of the image signals of the at least two test single frames when the respective image signal lies within a second value range complementary to the first value range.

5. The method according to claim 1, wherein the markers have an average time period for which the markers remain in the state in which the markers are configured to be imaged by the light microscope, and the interval at which the at least two test single frames are generated is in a range from one through three times the average time period.

6. The method according to claim 5, wherein the sensor elements have an exposure time, the exposure time being set approximately equal to the average time period for which the markers remain in the state in which the markers are configured to be imaged by the light microscope.

7. The method according to claim 1, wherein when the predetermined activation state is present, the predetermined activation state is repeatedly checked while reducing the interval at which the at least two test single frames are generated until the detected changes of the image signals no longer collectively exceed the predetermined quantity;

wherein the sensor elements have an exposure time, and the exposure time is set taking into account the interval at which the detected changes of the image signals no longer collectively exceed the predetermined quantity.

8. The method according to claim 1, wherein an image sequence of single frames is captured and the presence of the predetermined activation state is checked prior to the capturing of each single frame in the image sequence.

9. The method according to claim 8, wherein at least one of the at least two test single frames is used as one of the single frames of the image sequence when the presence of the predetermined activation state has been determined.

10. A light microscope for imaging a sample structure prepared with markers that are configured to be brought into a state in which the markers are configured to be imaged by the light microscope, the light microscope comprising:
a resolution limit;
an illumination system providing a beam of activation light, wherein the beam of activation light generates an active marker subset by bringing a portion of the markers into the state in which the markers are configured to be imaged by the light microscope;
an image detector arranged to receive light emitted by markers in the active marker subset, the image detector including a plurality of sensor elements each generating a respective image signal, wherein the image signals generated at a point in time collectively provide a single frame; and
a control unit connected to the image detector and configured to check for presence of a predetermined activation state in which markers in the active marker subset have an average distance from one another greater than a minimum distance predetermined by the resolution limit of the light microscope, wherein the control unit processes at least two test single frames generated at an interval and compares the at least two test single frames to one another in order to detect a change of the image signals between the at least two test single frames, and the control unit finds the presence of the predetermined activation state if the detected changes of the image signals collectively exceed a predetermined quantity.

* * * * *